United States Patent [19]

Weinstein et al.

[11] Patent Number: 4,525,540
[45] Date of Patent: Jun. 25, 1985

[54] CYCLIC ESTER DIENES, POLYMERIC AND OTHER DERIVATIVES THEREOF

[75] Inventors: Boris Weinstein; Edward Orton, both of Seattle, Wash.

[73] Assignee: Washington Research Foundation, Seattle, Wash.

[21] Appl. No.: 461,706

[22] Filed: Jan. 28, 1983

[51] Int. Cl.$^3$ .................................. C08F 224/00
[52] U.S. Cl. ........................ 525/327.2; 525/327.3; 526/266; 526/269
[58] Field of Search .................. 526/266, 269; 525/327.2, 327.3

[56] References Cited

U.S. PATENT DOCUMENTS

| | | | |
|---|---|---|---|
| 2,518,440 | 8/1950 | Joyce | 526/269 |
| 3,431,278 | 3/1969 | Forgione | 526/269 |
| 3,471,430 | 10/1969 | Zimmerman et al. | 526/266 |

*Primary Examiner*—Harry Wong, Jr.
*Attorney, Agent, or Firm*—Bertram I. Rowland

[57] ABSTRACT

Novel dibasic organic acid diesters of the dienol form of biacetyl and methods for their preparation are provided. The compounds find use as monomers in homo- and copolymers, and the resulting polymers may be further modified to produce a variety of products.

2 Claims, No Drawings

CYCLIC ESTER DIENES, POLYMERIC AND OTHER DERIVATIVES THEREOF

BACKGROUND OF THE INVENTION

1. Field of the Invention

There is continuing interest in the preparation of small polyfunctionalized organic compounds, which compounds may find use in a variety of applications. Of particular interest are novel monomers which can be used by themselves, or in conjunction with other monomers, to produce polymers having functionalities of interest. To prepare simple organic compounds suitable for commercial use, it is necessary to provide methods of preparation that provide high yields, ease of purification, and substantial absence of materials that might interfere with the utility of the compounds of interest. Furthermore, because of the wide variety of existing compounds, new compounds of significant interest are only rarely synthesized.

2. Description of the Prior Art

Scharf and Plum, Liebigs Ann. Chem., 1977, 27, describe the preparation of 4,5-dimethylene-1,3-dioxolan-2-one and its polymerization on heating. Steiner and Weinstein, Abstracts of the 178th National Meeting, American Chemical Society, OREN 187, Washington, D.C., 1979, describe the preparation of the aforementioned compound. U.S. Pat. No. 2,445,733, describes methylene dioxolanes.

SUMMARY OF THE INVENTION

Novel 1,2-dimethylene substituted cyclic esters, their substitution products, derivatives, particularly polymers thereof, as well as methods for preparing these compounds are provided. Particularly, the carbonate, thionocarbonate, and oxalate cyclic esters are prepared and used as monomers or reactants to prepare useful products.

DESCRIPTION OF THE SPECIFIC EMBODIMENTS

Cyclic diesters of dibasic carboxylic acids of from one to two carbon atoms and having vicinal methylenes, so as to define a butadiene, are provided. The compounds will have at least five carbon atoms and three chalcogen atoms of atomic number 8 to 16 (oxygen and sulfur) and will generally not exceed about 20 carbon atoms, usually having not more than about 18 carbon atoms. The compounds may be substituted or unsubstituted on the methylene carbon atoms, and there are no available sites for substitution on annular atoms.

For the most part, the monomeric compounds of this invention will have the following formula:

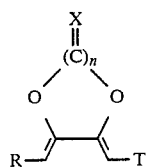

wherein:

n is 1 or 2;

X is a chalcogen, namely oxygen or sulfur, preferably being oxygen when n is 2 and sulfur when n is 1; and R and T are the same or different and are hydrogen or a substituent group bonded to the methylene through carbon, being a hydrocarbyl group of from 1 to 12, usually 1 to 8, more usually 1 to 6 carbon atoms or a heterosubstituted hydrocarbyl group having from 1 to 12 atoms and including 1 to 6 heteroatoms, which may be chalcogen, halogen, nitrogen, or the like. The choice of substituents will be governed by the manner of preparation. Where dehydrobromination is involved, the substituents will have to be stable under the conditions of the synthetic procedure.

"Hydrocarbyl" is an organic group composed solely of carbon and, as appropriate, hydrogen, and may be aliphatic, alicyclic, aromatic, or combinations thereof, being aliphatically saturated or unsaturated, normally having not more than about one site of unsaturation. "Heterosubstituted hydrocarbyl" groups have one or more hydrogen atoms substituted by a heteroatom, even including one carbon species such as cyano and carboxy.

Illustrative substituents on the methylenes include trifluoromethyl, methyl, phenyl, cyano, ethoxycarbonyl, methoxymethyl, etc.

The monomeric compounds of the subject invention may be prepared according to the following reaction scheme:

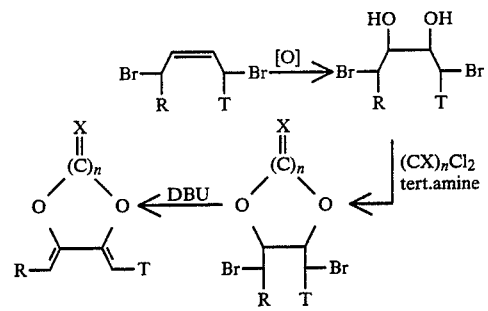

wherein the symbols have been defined previously.

The oxidation can be conveniently carried out employing osmium tetraoxide in the presence of N-methylmorpholine N-oxide. Other oxidants may also find use, such as permanganates, lead tetraacetate or other agents that form glycols directly. The 1,4-substituted-1,4-dibromo-2,3-butanediol may then be esterified employing an acyl dihalide, particularly dichloride, in the presence of a tertiary amine. Anhydrides may also find use.

The dehydrobromination may be employed with an amine base, particularly an amidine, where the nitrogens are free of hydrogen. Therefore, relatively strong nitrogen bases are desired. Of particular interest is the use of 1,8-diazabicyclo[5.4.0]undec-5-ene (DBU).

The subject monomers react to form both homo- and copolymers. Any of the ethylenic addition monomers may be employed with the subject monomers to form the copolymers. Illustrative monomers include styrene, acrylate esters, methacrylate esters, acrylonitrile, vinyl compounds, such as vinyl chloride, vinylidene chloride, vinyl acetate, maleic anhydride, ethylene, propylene, butadiene, isoprene, etc.

The subject monomers homopolymerize spontaneously at mild temperatures, particularly when neat. The subject compounds may be mixed with other monomers and will polymerize under well-known polymerizing conditions, such as free radical polymerization, anionic polymerization, and the like. The preferred mode of polymerization appears to be 1,4, so that the resulting functionality is a cyclic ester of an enediol. The enediol functionality is a versatile functionality having a number of different uses. Upon hydrolysis, the enediol can exist in either of two structures, the enediol or an acyloin structure. The acyloin may be used in redox reactions, either being reduced to the diol or being oxidized to the $\alpha,\beta$-diketone. Both the diol and diketone may be used as sites for cleavage, where the subject monomers have been employed as copolymers to oligomerize or polymerize with a different monomer, providing dialdehydes or diacids of varying molecular weight.

The polymers will for the most part have the following formula:

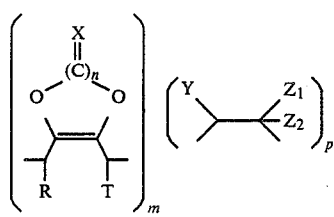

wherein:

R, T, X and n have been defined previously, and the remaining symbols are as defined as follows:

m is at least 1, usually being at least 2 or higher, the number depending to a degree on whether the polymer is a homopolymer or copolymer;

p may be 0, 1 or greater, depending upon whether the polymer is a homopolymer or copolymer, as well as upon whether the polymer is an alternating polymer or block copolymer, or the like, and m and p are 2 or greater;

$Z_1$ and $Z_2$ are the same or different and may be hydrogen, halogen, particularly of atomic number 9 to 35, more particularly of from atomic number 9 to 17, acyloxy of from 1 to 3 carbon atoms, alkoxy of from 1 to 3 carbon atoms, hydrocarbyl, particularly alkyl of from 1 to 2 carbon atoms or aryl of from 6 to 9 carbon atoms, carboxy, carboalkoxy, wherein the alkoxy group is of from 1 to 3 carbon atoms, cyano, etc., that is, those groups which provide for monomers capable of addition polymerization, either by cationic, anionic, or radical polymerization;

Y is normally hydrogen, but may be taken together with $Z_1$ to form a carboxylic acid anhydride group.

Both the homo- and copolymers can be hydrolyzed to form $\alpha$-hydroxyketone units and their salts which exist in the enediol form. The monomeric unit in the polymer will have the following formula:

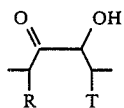

wherein the symbols have been defined previously. These compounds may be oxidized to the diketone or reduced to the vicinal diol.

The subject dimethylene cyclic esters may be used as starting materials for addition products, where various functionalities have been added to the annular carbon atoms. Nucleophilic reagents may be employed where the double bonds are protonated and the functionality becomes bound to the annular carbon atoms. Illustrative compounds include hydroxyl compounds, particularly alcohols and phenols, acyloxy groups, and the like. Mono- or polyols may also be employed, providing for both monomeric products and the formation of heteropolycyclics and condensation polymers, depending upon the nature of the hydroxylic compound.

The compounds described above have a wide variety of uses. Polymers having the glycol functionality may substitute for head-to-head vinyl alcohol polymers. Such polymers, as well as the $\alpha$-hydroxyketone polymers, may be crosslinked by a wide variety of bifunctional compounds, such as diacids, diisothiocyanates, diethers, etc., so as to form strong three-dimensional structures. The keto functionality may also be used for crosslinking, using diamines, hydrazines, and the like for crosslinking.

The $\alpha$-hydroxyketone can be treated with base to provide a substantial proportion of the functionality as the enediol. In this form, the compound may serve as a redox reagent capable of being reduced or oxidized, a chelating agent to provide ion-exchange, a metal catalyst, or the like. Incorporation of diketones into the polymer can provide linking arms as well as sites for chelation, for condensation with itself or other molecules to form cyclic molecules, for extending structures, or the like.

In the copolymers, the cyclic esters can provide for a particular degree of functionality which may be desired to provide properties to the polymer or to serve as a site for cleavage to provide for functionalized lower molecular weight compounds.

The subject polymers can be doped with tetracyanoethylene or a conducting metal ion to provide for semiconducting properties.

The monomeric compounds of this invention may be prepared with the simple starting material 1,4-dibromo-2-butene. The dibromobutenes and substituted-dibromobutenes may be hydroxylated with osmium tetroxide and N-methylmorpholine-N-oxide (Van Rheenen et al., Tetrahedron Lett. (1976) 23:1973; Whitesell, J. Am. Chem. Soc (1981) 103:3468) or with potassium permanganate (Neher, Helv. Chim. Acta. (1963) 46:1083). The resulting dibromodiols may then be esterified with the appropriate acyl halide, e.g. phosgene or oxalyl chloride, to form the cyclic dilactone. In addition to halides, carbonyl imidazoles may be employed (Corey and Winter, J. Am. Chem. Soc. (1963) 85:2667).

The halogen may then be removed by dehydrobromination, conveniently employing an amine base, more particularly a strong amine base, where the nitrogen is free of hydrogens. Of particular interest are amidines, more particularly amidines involved in a cyclic structure, such as 1,5-diazabicyclo[5.4.0]-undec-5-ene. The dibromide diester is combined with the base in an inert solvent, e.g. a haloalkane, such as dichloromethane and the product may be isolated by flash chromatography depending upon the particular product. It may be desirable to maintain the product in solution, particularly at mild temperatures, where spontaneous polymerization may occur.

The following examples are offered by way of illustration and not by way of limitation.

EXPERIMENTAL

Methods

IR spectra were recorded on Perkin-Elmer model 253 and 257 spectrometers. UV spectra were recorded on a Varian Superscan 3 spectrometer. 'H NMR spectra were measured on a Varian EM-360 spectrometer with $Me_4Si$ as the internal standard. Mass spectra were recorded on a VG 7070 mass spectrometer with an associated VG 2035 F/B data system. Melting points were observed on a Reichert hot stage microscope and are uncorrected.

Analytical thin-layer chromatography (t.l.c.) was performed on Merck Silica gel 60 F-254 plates. Flash chromatography employed Merck Silica gel 60 (230–400 mesh). Reactions performed under anhydrous conditions were conducted in flame-dried glassware under an inert atmosphere (argon). Commercially procured chemicals were purified by standard techniques before use. Elemental analyses were determined by Canadian Microanalytical Service Ltd., Vancouver B.C., Canada.

1. 4,5-Dimethylene-1,3-dioxolan-2-one

To a stirring solution of 4,5-dibromomethyl-1,3-dioxolan-2-one (2.14 g, 7.8 mmole) in anhydrous $CH_2Cl_2$ under argon at 20° C. was added 1,8-diazabicyclo[5.4.0]undec-5-ene (2.33 ml, 15.6 mmole) dropwise over 0.5 h. After stirring 5 h, the mixture was flash chromatographed ($CH_2Cl_2$ eluent) in its entirety giving 4,5-dimethylene-1,3-dioxolan-2-one as a $CH_2Cl_2$ solution: mp 46°–47° C.; IR (KBr) 3019, 1820, 1668, 1270, 1027 $cm^{-1}$; H NMR (CDCl$_3$) 5.02(s); GC/MS (70 eV) m/e (rel. intensity) 112.1 (38), 68.1 (15), 42.0 (100).

2. 4,5-Dimethyl-1,3-dioxol-2-one

The single flash column fraction (refer to step 1, above) of 4,5-dimethylene-1,3-dioxolan-2-one in $CH_2Cl_2$ (10 ml) was hydrogenated at 20° C./760 mm Hg in the presence of 5% Pd-C (25 mg) for 4 h. After filtration and solvent evaporation, flash chromatography (ethyl etherhexane eluent) of the crystalline residue gave dimethylvinylene carbonate as a colorless, crystalline solid (30 mg): mp 78°–79° C. [Litt. mp 78°–79° C.]; IR (KBr) 2965, 2935, 1795, 1732, 1238, 1188, 1017, 765 $cm^{-1}$; 'H NMR (CDCl$_3$) 2.08(s); MS $C_5H_6O_3$ calcd. 114.1024, obsd. 114.0304.

3. Tricarbonyl (4,5-dimethylene-1,3-dioxolan-2-one) iron

A solution of 4,5-dimethylene-1,3-dioxolan-2-one (12 mg, 0.1 mmole) and diiron nonacarbonyl (100 mg, 0.3 mmole) in degassed hexane (10 ml) under argon was refluxed 4 h then filtered and flash chromatographed (ethyl ether-hexane eluent). Sublimation of the eluate at 55° C./15 mm Hg gave tricarbonyl (4,5-dimethylene-1,3-dioxolan-2-one) iron as pale yellow needles (12 mg, 43%): mp 99°–100° C. [Litt. mp 88°–89° C.]; IR (KBr) 2050, 1995, 1982, 1807, 1295, 990 $cm^{-1}$; 'H NMR (CDCl$_3$) 2.55(d, J=6 Hz, 1H); GC/MS (70 eV) $C_8H_4FeO_6$ calcd. 252.0 obsd. 252.0.

4. 3,3-Diethoxy-2-butanone

A mixture of 4,5-dibromomethyl-1,3-dioxolan-2-one (2.07 g, 7.6 mmole) and 1,8-diazabicyclo[5.4.0]undec-5-ene (2.26 ml, 15.2 mmole) in $CH_2Cl_2$ (20 ml) was stirred at 20° C. for 5 h, then anhydrous ethanol (5.0 ml, 85 mmole) was added, and the resulting mixture was stirred at 20° C. for 10 h. Flash chromatography (ethyl ether-hexane eluent) of the reaction mixture yielded 3,3-diethoxy-2-butanone as a colorless liquid (110 mg, 10%): IR (AgCl) 2965, 1722, 1350, 1253, 1133, 1050, 954 $cm^{-1}$; 'H NMR (CDCl$_3$) 1.23 (m, 9 H), 2.28 (s, 3 H), 3.50(q, J=7.5 Hz, 4 H).

5. 4,5-Dimethoxy-4,5-dimethyl-1,3-dioxolan-2-one

A mixture of 4,5-dibromomethyl-1,3-dioxolan-2-one (1.21 g, 4.4 mmole) and 1,8-diazabicyclo[5.4.0]undec-5-ene (1.31 ml, 8.8 mmole) in $CH_2Cl_2$ (25.0 ml) was stirred at 20° C. for 4 h. Methanol (2.0 ml, 49 mmole) was then added and the mixture was stirred for 1 h at 20° C. Flash chromato graphy (ethyl ether-hexane eluent) of the mixture yielded 4,5-dimethyoxy-4,5-dimethyl-1,3-dioxolan-2-one as a colorless crystalline solid (0.208 g, 42%): mp 76°–77° C.; IR (KBr) 2980, 2945, 1803, 1790, 1358, 1279, 1167, 1023, 990 $cm^{-1}$; 'H NMR (CDCl$_3$) 1.55(s, 1 H), 3.48 (s, 1H); Anal. $C_7H_{12}O_5$ calcd. C 47.73, H 6.87, obsd. C47.69, H 6.49.

6. 4,5-Dimethylene-1,3-dioxolan-2-thione

A solution of threo-4,5-bis(bromomethyl)-1,3-dioxolan-2-thione (0.534 g, 1.8 mmole) and 1,8-diazabicyclo[5.4.0]undec-5-ene (0.55 ml, 3.6 mmole) in anhydrous $CH_2Cl_2$ (25 ml) was stirred for 4 h at 20° C., then flash chromatographed ($CH_2Cl_2$ eluent) giving 4,5-dimethylene-1,3-dioxolan-2-thione as a $CH_2Cl_2$ solution: mp 71° C.; IR (KBr) 3115, 3000, 1650, 1312, 1235, 1080, 949 $cm^{-1}$; 'H NMR (d$_6$-benzene) 4.22(d, J=4 Hz, 1H), 3.93(d, J=4 Hz, 1H), GC/MS (70 eV) m/e (rel. intensity) 128.1 (37), 68.1 (15), 42.0 (100).

7. Threo-4,5-bis(bromomethyl)-1,3-dioxolan-2-thione

A stirring solution of 1,4-dibromo-2,3-butadiol (1.95 g, 8.0 mmole) and N,N'-thiocarbonyldi-imidazole (1.40 g, 8.0 mmole) in anhydrous toluene (50 ml) was heated to 40° C. for 4 h. Flash chromatography (ethyl ether eluent) followed by recrystallization from hexane yielded threo-4,5-bis-(bromomethyl)-1,3-dioxolan-2-thione as a colorless crystalline compound (1.79 g, 77%): mp 86°–87° C.; IR (KBr) 2955, 1380, 1335, 1321, 1289, 1271, 1253, 1165, 1061, 995 $cm^{-1}$; 'H NMR (CDCl$_3$) 3.70(d, 2H), 5.10(t, 1H); Anal. $C_5H_6Br_2O_2S$ calcd. C 20.71, Br 55.11, obsd. C 20.88, Br 55.28.

8. Threo-5,6-bis(bromomethyl)-1,4-dioxan-2,3-dione

To a stirring solution of 1,4-dibromo-2,3-butadiol (874 mg, 3.5 mmole) and triethylamine (1.1 ml, 7.5 mmole) in anhydrous $CH_2Cl_2$ under argon at 20° C. was added dropwise over 0.5 h a solution of oxalyl chloride (0.31 ml, 3.5 mmole) in $CH_2Cl_2$ (10 ml). After stirring 3 h, the mixture was concentrated in vacuo (20° C./20 mm Hg), filtered, and flash chromatographed ($CH_2Cl_2$ eluent) to afford threo-5,6-bis(bromomethyl)-1,4-dioxan-2,3-dione as a colorless crystalline compound (817 mg, 77%): mp 76°–77° C.: IR (KBr) 3035, 2942, 1793, 1785, 1370, 1168, 1068 1051 $cm^{-1}$; 'H NMR (CD$_2$Cl$_2$) 3.70(d, J=4 Hz, 4H), 4.80 (t, J=2 Hz, 2H) Anal. $C_6H_6Br_2O_4$ calcd. C 23.87 Br 52.93, obsd. C 23.76, Br 58.29.

9. 5,6-Dimethylene-1,4-dioxan-2,3-dione

To a stirring solution of threo-5,6-bis(bromomethyl)-1,4-dioxan-2,3-dione (380 mg, 1.2 mmole) in anhydrous $CH_2Cl_2$ (25 ml) at 20° C. under argon was added dropwise 1,8-diazabicyclo[5.4.0]undec-5-ene (0.38 ml, 2.4 mmole) over 15 min. After stirring 4 h, the entire solution was flash chromatographed (CH$_2$Cl$_2$ eluent) giving 5,6-dimethylene-1,4-dioxan-2,3-dione as a CH$_2$Cl$_2$ solution: mp 44° C.; IR (CH$_2$Cl$_2$) 2862, 1851, 1838, 1663, 1600, 1380, 1110, 1078, 1028, 853 cm$^{-1}$; $^1$H NMR (CD$_2$Cl$_2$) 4.85(d, J=4 Hz, 1H), 5.10(d, J=4 Hz, 1H), GC/MS (70 eV) m/e (rel. intensity) 112.1 (38), 68.1 (18), 42.0 (100).

10. Polymerization of 4,5-dimethylene-1,3-dioxolan-2-one

The flash chromatographic fractions containing 4,5-dimethylene-1,3-dioxolan-2-one in CH$_2$Cl$_2$ (refer to step 1, above) were combined and refluxed under argon. After three days at reflux, t.l.c. no longer revealed the presence of the 4,5-dimethylene-1,3-dioxolan-2-one, and the solution contained a white precipitate. Filtration followed by washing with acetone, and drying in vacuo (20° C./0.01 mm Hg) yielded poly(4,5-dimethylene-1,3-dioxolan-2-one) as a white, amorphous powder: mp 210°–220° C. (decomposed without melting); Anal. (C$_5$H$_4$O$_3$)$_n$ calcd. C 53.58, H 3.60, obsd. C 50.81, H 3.56.

11. Polymerization of 4,5-Dimethylene-1,3-dioxolan-2-thione

The flash chromatographic fractions containing 4,5-dimethylene-1,3-dioxolan-2-thione in CH$_2$Cl$_2$ (refer to step 10, above) were combined and refluxed under argon. After three days at reflux, t.l.c. no longer indicated the presence of 4,5-dimethylene-1,3-dioxolan-2-thione, and the solution contained a white precipitate. Filtration followed by washing with acetone, and drying in vacuo (20° C./0.01 mm Hg) yielded poly(4,5-dimethylene-1,3-dioxolan-2-thione) as a white, amorphous powder: mp 170°–200° (decomposed without melting); Anal. (C$_5$H$_4$O$_2$S)$_n$ calcd. C 46.86, S 25.02, obsd. C 46.95, S 24.90.

12. Hydrolysis of Poly(4,5-dimethylene-1,3-dioxolan-2-one)

Poly(4,5-dimethylene-1,3-dioxolan-2-one) (75 mg) was dissolved in 5% aqueous NaOH (50 ml) with stirring. The resulting clear solution was treated with about 50 ml of 5% aqueous HCl to bring to the pH to 7.0. No precipitate was observed. Upon being acidified to pH>1.0, the solution deposited an amorphous, offwhite substance ($\alpha$-hydroxyketone polymer).

13. Hydrolysis of Poly(4,5-dimethylene-1,3-dioxolan-2-thione)

Poly(4,5-dimethylene-1,3-dioxolan-2-thione) (105 mg) was dissolved in 5% aqueous NaOH (50 ml) with stirring to form a clear solution. Acidification of that solution with 6N HCl resulted in the evolution of hydrogen sulfide. $\alpha$-Hydroxyketone polymer was observed to precipitate when the pH of the solution was greater than 1.0.

14. Reaction of Diethylamine with 4,5-Dimethylene-1,3-dioxolan-2-one

To a single flash column fraction (refer to atep 1, above) of 4,5-dimethylene-1,3-dioxolan-2-one in CH$_2$Cl$_2$ at 20° C. under argon was added dropwise with stirring diethylamine (1.0 ml, 9.6 mmole). After stirring for 10 min, the solvent was removed in vacuo (20° C./15 mm Hg), and the residue was flash chromatographed (ethyl ether eluent) to yield 3-oxobut-2-en-2-yl-N,N-diethyl carbamate as a colorless liquid (155 mg): IR (AgCl) 3120, 2992 to 2780, 1702, 1640, 1421, 1268, 1123, 1157, 1130, 1055, 988, 915, 791, 760; $^1$H NMR (CDCl$_3$) 1.20(t, 6H), 2.33(s, 3H), 3.34(q, 4H), 5.52(d, J=2.5 Hz, 1H), 5.83(d, J=2.5 Hz, 1H).

15. Polymerization of 5,6-Dimethylene-1,4-dioxan-2,3-dione

The flash chromatographic fractions containing 5,6-dimethylene-1,4-dioxan-2,3-dione in CH$_2$Cl$_2$ (refer to step 9, above) were combined and refluxed under argon. After two days, t.l.c. no longer indicated the presence of 5,6-dimethylene-1,4-dioxan-2,3-dione, and a white precipitate was evident. Filtration followed by washing with acetone gave poly(5,6-dimethylene-1,4-dioxan-2,3-dione) as a white, amorphous powder.

16. 4,5-Dibenzyl-1,3-dioxolan-2-one

Phosgene gas was slowly bubbled into a solution of 1,4-diphenyl-2,3-butanediol (Neher (1963) Hel. Chim. Acta. 46:1083) (96 mg, 0.4 mmole) and triethylamine (0.16 ml, 1 mmole) in anhydrous ethyl ether (75 ml). After 15 min, the phosgene addition was stopped, the solution filtered, and the solvent removed in vacuo (20° C./60 mm Hg) leaving a crystalline residue, which was flash chromatographed (CH$_2$Cl$_2$ eluent) affording 4,5-dibenzyl-1,3-dioxolan-2-one as a colorless, crystalline compound (98 mg, 94%): mp 155°–156° C.; IR (KBr) 3020, 1783, 1200, 1166, 1150, 1092, 1067, 1030, 765, 755, 703 cm$^{-1}$; $^1$H NMR (CDCl$_3$) 2.88(m, 4H), 4.55(t, J=3 Hz, 2H), 7.33(m, 10H); MS (70 eV) C$_{17}$H$_{16}$O$_3$ calcd. 268.3235 obsd. 268.1096.

17. 4,5-Dibenzylidene-1,3-dioxolan-2-one

N-Bromosuccinimide (0.1033 g, 0.58 mmole) was added to a refluxing solution of 4,5-dibenzyl-1,3-dioxolan-2-one (75 mg, 0.28 mmole) in CCl$_4$ (30 ml) under argon. The refluxing mixture was irradiated with a 75 watt unfrosted tungsten light for 0.5 h. Refluxing was continued for 3 h, then the solution was cooled, filtered, and the solvent removed in vacuo (20° C./15 mm Hg). Flash chromatography (ethyl ether-hexane eluent) gave 4,5-dibenzylidene-1,3-dioxolan-2-one (47 mg, 63%): mp115° C. (rapid heating); IR (AgCl) 3023, 1812, 1493, 1453, 1365, 1156, 1087, 910, 697 cm$^{-1}$; $^1$H NMR (CDCl$_3$) 7.39(s, 10H), 4.95(s, 2H).

In accordance with the subject invention, novel cyclic diesters of diabasic carboxylic acids of from one to two carbon atoms and having vicinal methylenes are provided. The diesters may be reacted with themselves or other monomers to form homo- and copolymers, respectively. Both the homo- and copolymers, in turn, may be hydrolyzed and will exist as either an enediol or acyloin structure.

Although the foregoing invention has been described in some detail by way of illustration and example for purposes of clarity of understanding, it will be obvious that certain changes and modifications may be practiced within the scope of the appended claims.

What is claimed is:

1. A polymer having the formula:

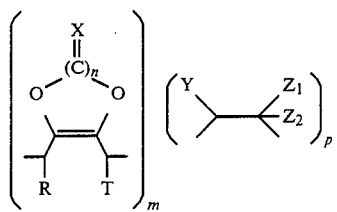

wherein:

n is 1 or 2;

X is sulfur when n is 1 and oxygen when n is 1 or 2; and

R and T are the same or different, being hydrogen, a hydrocarbyl group having from 1 to 12 carbon atoms, or a 1 to 6 heteroatom substituted hydrocarbyl group having from 1 to 12 carbon atoms, wherein said heteroatoms are chalcogen, halogen, or nitrogen;

m is at least 1 and when m is 1, p is at least 2;

p is 0 or greater, and m+p are two or greater;

$Z_1$ and $Z_2$ are the same or different, being hydrogen, halogen, acyloxy of from 1 to 3 carbon atoms; alkoxy of from 1 to 3 carbon atoms, hydrocarbyl, carboxy, cyano, or carboalkoxy wherein the alkoxy group is from 1 to 3 carbon atoms; and Y is hydrogen or taken together with $Z_1$ and the ethylene to which they are attached to form a maleic anhydride group.

2. A polymer as in claim 1, wherein the heteroatoms are chalcogen.

* * * * *